US00PP35796P2

(12) United States Plant Patent
Scheiber

(10) Patent No.: US PP35,796 P2
(45) Date of Patent: May 7, 2024

(54) ***HYDRANGEA* PLANT NAMED '1925QUERREP'**

(50) Latin Name: *Hydrangea quercifolia*
Varietal Denomination: 1925querrep

(71) Applicant: The Conard Pyle Company, West Grove, PA (US)

(72) Inventor: Sloane Michele Scheiber, West Grove, PA (US)

(73) Assignee: The Conard Pyle Company, West Grove, PA (US)

( * ) Notice: Subject to any disclaimer, the term of this patent is extended or adjusted under 35 U.S.C. 154(b) by 0 days.

(21) Appl. No.: 18/203,760

(22) Filed: May 31, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP27,879 P3 * 4/2017 Branhagen ..... A01H 5/02
Plt./250

OTHER PUBLICATIONS

Star Roses and Plants Autumn Reprise *Hydrangea*, retrieved on Sep. 12, 2023 at https://www.starrosesandplants.com/plants/autumn-reprise-hydrangea/, 4 pp. (Year: 2023).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of *Hydrangea* plant, referred to by its cultivar name, '1925querrep', is disclosed. The new variety forms attractive, white colored inflorescences which age to pink. Repeat blooming is provided. Light to medium green foliage is displayed. A moderately vigorous, well-branched upright and compact growth habit is displayed. The new variety is well suited for providing attractive ornamentation in the landscape.

1 Drawing Sheet

Latin name of genus and species of plant claimed: *Hydrangea quercifolia.*

Variety denomination: '1925querrep'.

STATEMENT REGARDING PRIOR DISCLOSURES BY THE INVENTOR

The first offer for sale of the new variety was June 2022, in the United States of America. The first offer for sale of the new variety was by an inventor or another who obtained the new variety directly or indirectly from an inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of *Hydrangea* plant of the present invention was discovered through a controlled program during October 2012, at Cochranville, Pennsylvania. The objective of the controlled program was the development of *Hydrangea* cultivars that have improved form, flowering, and disease resistance. The new *Hydrangea* cultivar is the result of open pollination. The female (seed) parent of the new cultivar is 'Amethyst', not patented. The male (pollen)

parent of the new cultivar is unknown. The new cultivar was discovered and selected as a single flowering plant within the progeny of the above stated open pollination during July 2017, in a controlled environment in Cochranville, Pennsylvania.

The new variety has been found to undergo asexual propagation in Cochranville, Pennsylvania by terminal stem cuttings since August 2017. Asexual propagation by terminal stem cuttings in Cochranville, Pennsylvania has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of *Hydrangea* plant of the present invention possesses the following combination of characteristics:

(a) forms white colored inflorescences that age to pink,
(b) provides repeat flowering,
(c) exhibits light to medium green colored foliage, and
(d) displays a moderately vigorous, well-branched upright and compact growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Amethyst' variety (i.e., the seed parent) forms white colored inflorescences that age to wine red, whereas the new variety forms white colored inflorescences that age to pink. In addition, the new variety reblooms, whereas the 'Amethyst' variety blooms only once per growth season and the new variety has better resistance to leaf spot compared to the 'Amethyst' variety. Moreover, the new variety can be readily distinguished from other similar non-parental varieties. For example, the 'JoAnn' variety (U.S. Plant Pat. No. 27,879) have a less upright and less dense growth habit compared to the new variety. In addition, the new variety reblooms, whereas the 'JoAnn' variety blooms only once per growth season and the new variety has less susceptibility to leaf spot compared to plants of 'JoAnn'.

The new variety has been named '1925querrep'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. Colors in the photograph differ slightly from the color values cited in the detailed description, which accurately describes the colors of '1925querrep'. The *Hydrangea* plants of the new variety were approximately four years of age and were observed during June 2022, while growing in a field at Cochranville, Pennsylvania, U.S.A.

The drawing sheet illustrates plants of the new variety displaying the overall growth and flowering habit.

DETAILED BOTANICAL DESCRIPTION

The chart used in the identification of the colors is that of The Royal Horticultural Society (The R.H.S. Colour Chart, 2015 edition), London, England. The color values were determined in July 2022, under natural light conditions in Cochranville, Pennsylvania. The terminology which precedes reference to the chart has been added to indicate the corresponding color in more common terms and The R.H.S. Colour Chart designation used herein represents the closest color observed on the majority of the specified botanical feature. The description is based on the observation of plants produced from cuttings from stock plants and grown in three-gallon containers utilizing a soilless growth medium for 1 year in an outdoor nursery in Cochranville, Pennsylvania. Measurements and numerical values represent averages of typical plants.

Botantical classification: *Hydrangea quercifolia* cultivar '1925querrep'.

Propagation:

*Type cutting.*—Terminal stem cuttings.

*Time to initiate roots during the summer.*—Approximately 28 days.

*Time to produce a rooted young plant during the summer.*—Approximately four months.

*Root description.*—White, fine, and fibrous.

*Rooting habit.*—Freely branching and dense.

Plant description:

*Commercial crop time.*—Approximately 12 months from a rooted cutting to finish in a 3-gallon pot.

*Growth habit and general appearance.*—Deciduous shrub, upright and outwardly spreading compact plant habit; strong and sturdy lateral branches; freely branching dense habit; moderately vigorous growth habit — approximately 18 inches of growth per season, on average.

*Hardiness.*—USDA Zone 5 (−20° F. to −15° F.).

*Size.*—Height from soil level to top of plant plane: Approximately 75.0 cm. Width: Approximately 90.0 cm.

*Branching habit.*—Freely branching. Pinching enhances branching. Quantity of lateral branches per plant: Approximately 4.

*Branch.*—Shape: Rounded. Strength: Strong. Length: Approximately 42.0 cm. Diameter: Approximately 5.0 mm. Length of central internode: Approximately 6.0 cm. Texture of young stem: Glabrous. Texture of mature stem: Woody. Color of young stem: Greyed-Orange Group 164A. Color of mature stem: Greyed-Orange Group 177A. Stem's lenticel diameter: Typically between 1 mm to 2 mm. Stem's lenticel shape: Round/circular. Stem's lenticel color: Greyed-Orange Group 165C. Stem's lenticel surface texture: Immature is cinerous; mature including exfoliating bark is papyraceous. Stem's lenticel exfoliating bark color: Greyed-Orange Group 165C.

Foliage description:

*General description.*—Quantity of leaves per lateral branch: Typically 8 to 12. Fragrance: None detected. Form: Simple. Arrangement: Opposite.

*Leaves.*—Aspect: Flat. Shape: Ovate. Margin: Lobed with serrulation. Number of leaf lobes: 5 per leaf. Apex: Acuminate. Base: Obtuse. Venation pattern: Pinnate. Length of mature leaf: Approximately 13.0 cm to 19.0 cm. Width of mature leaf: Approximately 9.5 cm to 12.0 cm. Texture of upper surface: Leathery; pubescent. Texture of lower surface: Coarse; pubescent. Color of upper surface of young foliage: Yellow-Green Group 147B with indistinguishable venation. Color of lower surface of young foliage: Green Group 138C with indistinguishable venation. Color of upper surface of mature foliage: Green Group 137A with venation of Green Group 139D. Color of lower surface of mature foliage: Yellow-Green Group 147B with venation of Yellow-Green Group 145A. Dormant terminal leaf bud shape: Conical, with two pairs of decussate leaves. Dormant terminal leaf bud size: Typically between 2.4 cm to 3.3 cm in length and approximately 1.0 cm in diameter. Dormant terminal leaf bud color: a color between Greyed-Orange Group N167D and 165B. Fall foliage colors: Include shades of plum and royal burgundy, N77A, 183A, 185A, and 187A.

*Petiole.*—Length: Approximately 6.0 cm. Diameter: Approximately 4.0 mm. Texture: Pubescent. Color upper surface: Greyed-Orange Group 176D. Color lower surface: Yellow-Green Group 145B.

Flowering description:

*Flowering habit.*—Plants flower continuously throughout the summer in Cochranville, Pennsylvania.

*Lastingness of individual inflorescence on the plant.*—Persistent, but color changes over time.

Inflorescence description:

*General description.*—Type: Single sterile and fertile flowers arranged on large terminal panicles. Quantity per plant: One per lateral or sublateral stem. Fragrance: Strongly fragrant; pleasant. Aspect: Face upward and outward. Height: Approximately 14.0 cm. Width: Approximately 11.0 cm. Shape: Conical. Quantity of fertile florets per inflorescence: Approximately 320. Quantity of sterile florets per inflorescence: Approximately 32. Conspicuousness of the fertile flower within the inflorescence: weak to medium.

Floret description:

*Sterile florets, bud.*—Shape: Globular. Length: Approximately 3.0 mm. Diameter: Approximately 2.0 mm. Color: Yellow-Green Group 154C.

*Sterile florets.*—Depth: Approximately 2.0 mm. Diameter: Approximately 3.5 cm.

*Sterile florets, sepals.*—Quantity per flower (petal number): Four in a single whorl. Shape: Orbicular. Margin: Entire. Apex: Obtuse. Base: Cuneate to rounded. Length: Approximately 1.5 cm. Width: Approximately 1.4 cm. Attitude: horizontal. Intensity of overlapping: weak. Texture, upper surface: Smooth, Glabrous. Texture, lower surface: Coarse, glabrous. Color of upper and lower surfaces when first open: Yellow Group 4D. Color when fully mature/fully open: 155A. Color when fading or aging: 59C, pink coloration covers the entire inflorescence, and pink coloration typically starts to develop in middle of July.

*Sterile florets, pedicel.*—Strength: Strong. Angle: About 20° to 40° from vertical. Length: Approximately 2.5 cm. Diameter: Approximately 1.0 mm. Texture: Smooth. Color: Yellow-Green Group 145C.

*Fertile florets, bud.*—Shape: Obovate. Length: Approximately 2.0 mm. Diameter: Approximately 1.0 mm. Color: Yellow-Green Group 150D.

*Fertile florets.*—Depth: 4.0 mm. Diameter: 8.0 mm.

*Fertile floret petals.*—Arrangement: Five in a single whorl. Length: Approximately 1.0 mm. Width: Approximately 0.5 mm. Shape: Elliptic. Apex: Obtuse. Base: Cuneate. Margin: Entire. Texture of upper and lower surfaces: Smooth, glabrous. Color: When opening, upper and lower surfaces: Yellow-Green Group 150D.

*Fertile floret sepals.*—Arrangement: Five in a single whorl. Length: Approximately 0.5 mm. Width: Approximately 0.5 mm. Shape: Subulate. Apex: Acute. Base: Cuneate. Margin: Entire. Texture of upper and lower surfaces: Smooth, glabrous. Color: When opening and fully opened, upper and lower surfaces: Yellow-Green Group 144C.

*Fertile florets, pedicel.*—Strength: Strong. Angle: About 20° to 45° from vertical. Length: Approximately 5.0 mm. Diameter: Approximately 1.0 mm. Texture: Pubescent. Color: Greyed-Orange Group 176A.

Reproductive organs:

*Fertile flowers.*—Stamens: Quantity per flower: About ten. Filament length: Approximately 4.0 mm. Filament color: White Group 155D. Anther shape: Round. Anther length: About 0.5 mm. Anther color: Greyed-Orange Group 166D. Pollen Amount: None Observed. Pistil Number: About three. Pistil length: Approximately 3.0 mm. Stigma shape: Round. Stigma color: White Group 155D. Style length: Approximately 2.0 mm. Style color: White Group 155D. Ovary color: Green Group 138B.

*Sterile flowers.*—Stamens: Quantity per flower: About six. Filament length: Approximately 1.0 mm. Filament color: Yellow-Green Group 145D. Anther shape: Round. Anther length: About 1.0 mm. Anther color: Greyed-Orange Group 164C. Pollen Amount: None Observed. Pistil Number: One. Pistil length: Approximately 2.0 mm. Stigma shape: Round. Stigma color: Yellow-Green Group 145C. Style length: Approximately 1.0 mm. Style color: Yellow-Green Group 145C.

Development:

*Seed and fruit production.*—Neither seed nor fruit production has been observed.

*Disease and pest resistance.*—Very good resistance to leaf spot (*Cercospora hydrangeae*). Resistance to pests common to *Hydrangea* has not been observed.

The new '1925querrep' variety has not been observed under all possible environmental conditions to date. Accordingly, it is possible that the phenotype may vary somewhat with variations in the environment, such as temperature, light intensity, and day length, without, however, any variance in genotype.

I claim:

1. A new and distinct variety of *Hydrangea* plant named '1925querrep' characterized by the following combination of characteristics:

(a) forms white colored inflorescences that age to pink,
(b) provides repeat flowering,
(c) exhibits light to medium green colored foliage, and
(d) displays a moderately vigorous, well-branched upright and compact growth habit;

substantially as herein shown and described.

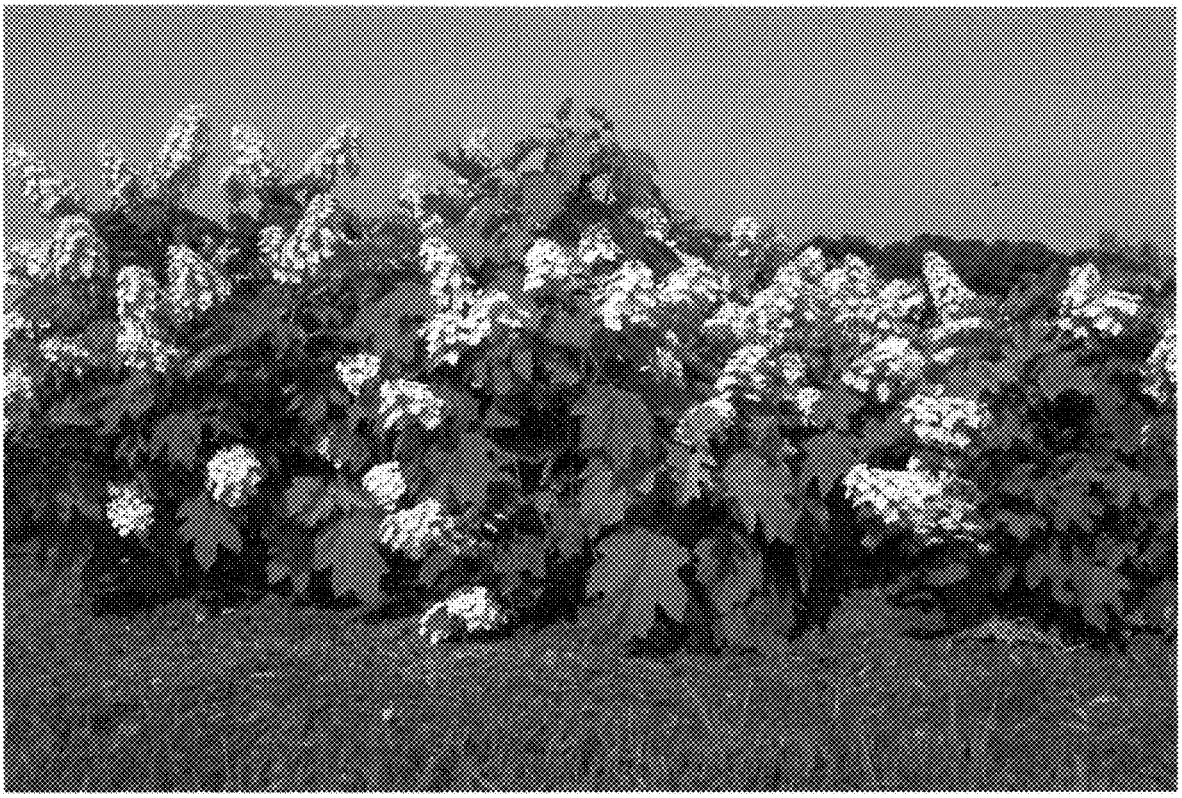

* * * * *